United States Patent
Ramadorai

(10) Patent No.: US 12,178,528 B2
(45) Date of Patent: Dec. 31, 2024

(54) SURGICAL ROBOTIC SYSTEMS AND METHODS OF TRACKING USAGE OF SURGICAL INSTRUMENTS THEREOF

(71) Applicant: Covidien LP, Mansfield, MA (US)

(72) Inventor: Arvind Ramadorai, Lexington, MA (US)

(73) Assignee: Covidien LP, Mansfield, MA (US)

(*) Notice: Subject to any disclaimer, the term of this patent is extended or adjusted under 35 U.S.C. 154(b) by 975 days.

(21) Appl. No.: 17/272,720

(22) PCT Filed: Sep. 9, 2019

(86) PCT No.: PCT/US2019/050129
§ 371 (c)(1),
(2) Date: Mar. 2, 2021

(87) PCT Pub. No.: WO2020/055707
PCT Pub. Date: Mar. 19, 2020

(65) Prior Publication Data
US 2021/0212784 A1     Jul. 15, 2021

Related U.S. Application Data

(60) Provisional application No. 62/731,423, filed on Sep. 14, 2018.

(51) Int. Cl.
*A61B 34/20* (2016.01)
*A61B 34/30* (2016.01)
(Continued)

(52) U.S. Cl.
CPC .............. *A61B 34/35* (2016.02); *A61B 34/20* (2016.02); *A61B 34/30* (2016.02); *A61B 34/37* (2016.02);
(Continued)

(58) Field of Classification Search
CPC ......... A61B 34/20; A61B 34/35; A61B 34/37; A61B 2034/2065; A61B 2090/0803;
(Continued)

(56) References Cited

U.S. PATENT DOCUMENTS 6,132,368 A    10/2000   Cooper
6,206,903 B1   3/2001   Ramans
(Continued)

FOREIGN PATENT DOCUMENTS

WO   WO-2017011646 A1 *   1/2017   .......... G06Q 10/087
WO   2017208678 A1   12/2017

OTHER PUBLICATIONS

European Search Report dated May 16, 2022, issued in corresponding EP Appln. No. 19858955, 9 pages.
(Continued)

*Primary Examiner* — Julian W Woo
*Assistant Examiner* — Cherie M Poland
(74) *Attorney, Agent, or Firm* — Carter, DeLuca & Farrell LLP

(57) ABSTRACT

A method of tracking usage of a robotic surgical instrument includes capturing an image of a surgical instrument with an imager during a robotic surgical procedure, identifying a type of the surgical instrument based on the image of the surgical instrument, determining a degree of usage of the surgical instrument based on data acquired by at least one sensor, and determining a stage in a life cycle of the surgical instrument based on the type of surgical instrument identified and the degree of usage determined.

19 Claims, 3 Drawing Sheets

(51) Int. Cl.
*A61B 34/35* (2016.01)
*A61B 34/37* (2016.01)
*A61B 90/96* (2016.01)
*G06V 20/64* (2022.01)
*G16H 20/40* (2018.01)
*G16H 40/40* (2018.01)
*G16H 40/63* (2018.01)
*A61B 90/00* (2016.01)

(52) U.S. Cl.
CPC ............ *G06V 20/64* (2022.01); *G16H 20/40* (2018.01); *G16H 40/40* (2018.01); *G16H 40/63* (2018.01); *A61B 2034/2065* (2016.02); *A61B 2090/0803* (2016.02); *A61B 2090/0805* (2016.02); *A61B 90/96* (2016.02)

(58) Field of Classification Search
CPC ............ A61B 2090/0805; A61B 90/96; G16H 20/40; G16H 40/40; G16H 40/63; G06V 20/64

See application file for complete search history.

(56) References Cited

U.S. PATENT DOCUMENTS

| | | | |
|---|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |

(56) References Cited

U.S. PATENT DOCUMENTS

| | | |
|---|---|---|
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,628,518 B2 * | 1/2014 | Blumenkranz ........ A61B 34/71 606/1 |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 * | 4/2018 | Blumenkranz ........ A61B 90/10 |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |

(56) References Cited

U.S. PATENT DOCUMENTS

| | | |
|---|---|---|
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2010/0087835 A1* | 4/2010 | Blumenkranz ........ A61B 34/30 606/130 |
| 2010/0176925 A1 | 7/2010 | Tethrake et al. |
| 2014/0100588 A1* | 4/2014 | Blumenkranz ........ A61B 34/35 606/130 |
| 2015/0164606 A1 | 6/2015 | Jacobs et al. |
| 2018/0071033 A1 | 3/2018 | Zhao et al. |

OTHER PUBLICATIONS

International Search Report dated Dec. 27, 2019, issued in corresponding international appln No. PCT/US2019/050129, 16 pages.

\* cited by examiner

SURGICAL ROBOTIC SYSTEMS AND METHODS OF TRACKING USAGE OF SURGICAL INSTRUMENTS THEREOF

BACKGROUND

Robotic surgical systems have been used in minimally invasive medical procedures. Some robotic surgical systems include a console supporting a surgical robotic arm and a surgical instrument or at least one end effector (for example, forceps or a grasping tool) mounted to the robotic arm. The robotic arm provides mechanical power to the surgical instrument for its operation and movement. Each robotic arm may include an instrument drive unit that operatively supports the surgical instrument.

Typically, the surgical instruments operated by a robotic surgical system have a limited number of uses. Determining when the useful life of the surgical instrument has expired is desired for safety and surgical effectiveness. Accordingly, a need exists for a means for accurately determining when a surgical instrument should be decommissioned.

SUMMARY

In accordance with an aspect of the present disclosure, a method of tracking usage of a robotic surgical instrument includes capturing an image of a surgical instrument with an imager during a robotic surgical procedure, identifying a type of the surgical instrument based on the image of the surgical instrument, determining a degree of usage of the surgical instrument based on data acquired by at least one sensor, and determining a stage in a life cycle of the surgical instrument based on the type of surgical instrument identified and the degree of usage determined.

Some methods may further include determining if the surgical instrument is performing a surgical task based on the image of the surgical instrument.

In some aspects, determining if the surgical instrument is performing a surgical task includes correlating the image of the surgical instrument with the data acquired by the at least one sensor of the surgical instrument.

In aspects, the surgical task may include the surgical instrument acting on tissue.

In other aspects, the degree of usage of the surgical instrument may be determined only when the surgical instrument is acting on tissue.

Some methods may further include assigning a value to the surgical task performed by the surgical instrument corresponding to the degree of usage of the surgical instrument.

In some aspects, the value assigned to the surgical task performed by the surgical instrument may be selected based on an amount of force applied to tissue by the surgical instrument during the surgical task.

Some methods may further include determining a duration of time the surgical task is performed by the surgical instrument at the assigned value.

Other methods may further include displaying on a display the stage in the life cycle of the surgical instrument.

In another aspect of the present disclosure, a robotic surgical system is provided and includes a robotic arm, a surgical instrument configured to be coupled to and operated by the robotic arm, an imager configured to capture an image of the surgical instrument during a surgical procedure, and a control device in communication with the imager. The control device is configured to identify a type of the surgical instrument based on the image of the surgical instrument captured by the imager, determine a degree of usage of the surgical instrument based on data acquired by at least one sensor associated with the surgical instrument, and determine a stage in a life cycle of the surgical instrument based on the type of the surgical instrument identified and the degree of usage determined.

In aspects, the control device may be further configured to determine when the surgical instrument is performing a surgical task based on the image of the surgical instrument.

In other aspects, the surgical task may include the surgical instrument acting on tissue.

In further aspects, the control device may be configured to determine the degree of usage of the surgical instrument only when the surgical instrument is acting on tissue.

In some aspects, the control device may be further configured to assign a value to the surgical task performed by the surgical instrument corresponding to the degree of usage of the surgical instrument.

In aspects, the value assigned to the surgical task performed by the surgical instrument may be selected by the control device based on an amount of force applied to tissue by the surgical instrument during the surgical task.

In other aspects, the control device may be further configured to determine a duration of time the surgical task is performed by the surgical instrument at the assigned value.

In further aspects, the control device may be further configured to display on a display the stage in the life cycle of the surgical instrument.

In some aspects, the imager may be a camera or an imaging modality.

In aspects, the surgical instrument may be a surgical stapler.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
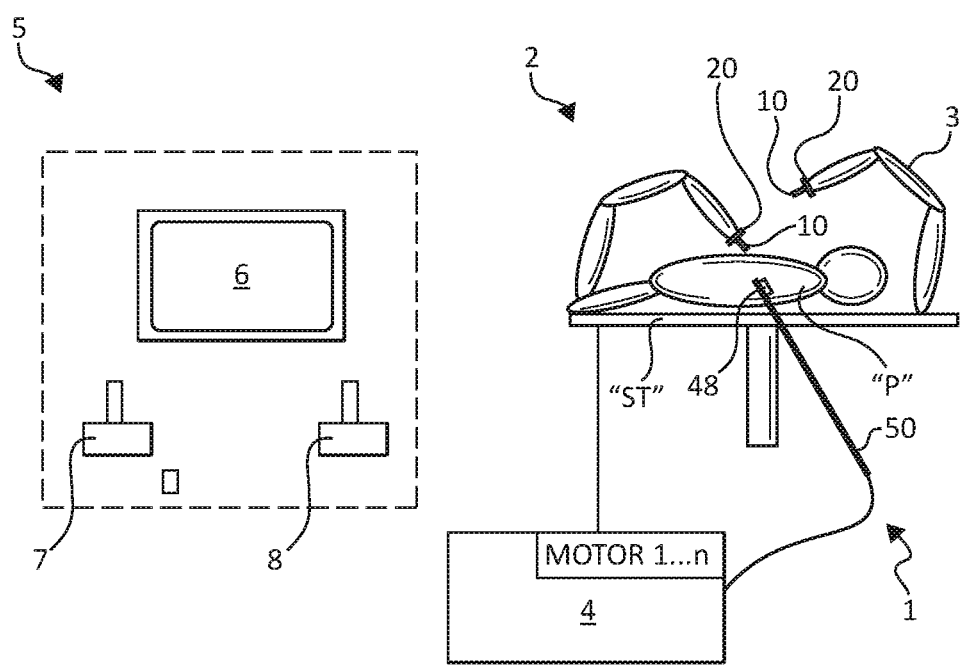
FIG. 1 is a schematic illustration of a robotic surgical system in accordance with the present disclosure.

Embodiments of the presently disclosed robotic surgical systems and methods of using such robotic surgical systems, are described in detail with reference to the drawings, in which like reference numerals designate identical or corresponding elements in each of the several views. As used herein the term "distal" refers to that portion of the robotic surgical system that is closer to the patient, while the term "proximal" refers to that portion of the robotic surgical system that is farther from the patient.

As will be described in detail below, a method of tracking usage of a surgical instrument of a surgical robotic system is provided. The method utilizes a camera of the robotic surgical system or a camera within an operating room to capture images of the surgical instrument in real-time during the surgical procedure. Based on the images captured by the camera, a control device of the surgical robotic system determines when the surgical instrument is actually being used to complete a surgical task (e.g., acting on tissue of a patient) as opposed to merely being moved in space without making contact with tissue of a patient. Sensors in the surgical instrument determine the forces applied by the surgical instrument on the tissue and send the determined forces to the control device. The control device then determines a degree of cumulative usage of the surgical instrument based on the amount of time the surgical instrument is experiencing the forces during each surgical task. If it is determined that the cumulative usage of the surgical instrument is beyond a predetermined usage limit, the control device may prevent further actuation of the surgical instrument. In some aspects, a display may provide a clinician with a visual indication of the degree of usage of the surgical instrument to allow a clinician to make the determination of whether to cease use of the surgical instrument.

Figure 2A:
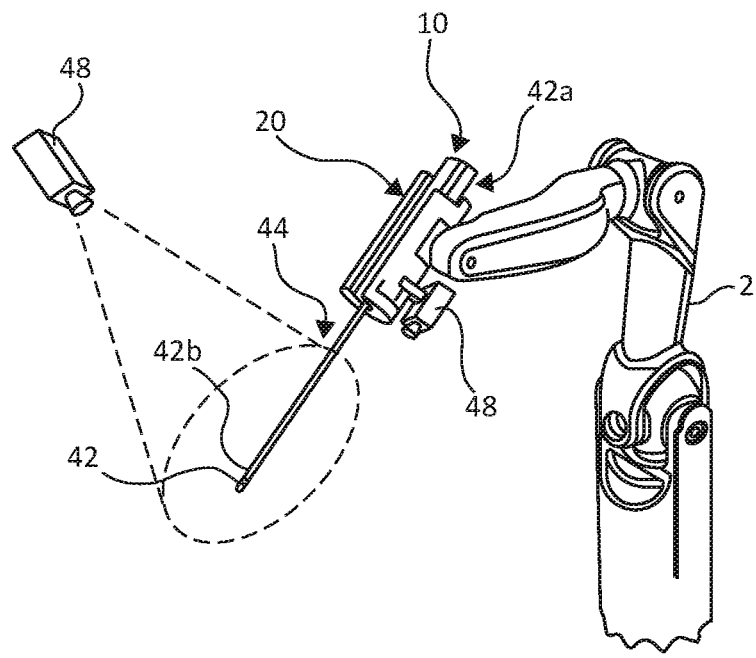
FIG. 2A is a perspective view of the robotic surgical system of FIG. 1, including a robotic arm, an instrument drive unit coupled to an end of the robotic arm, and a surgical instrument coupled to the instrument drive unit.
Figure 2B:
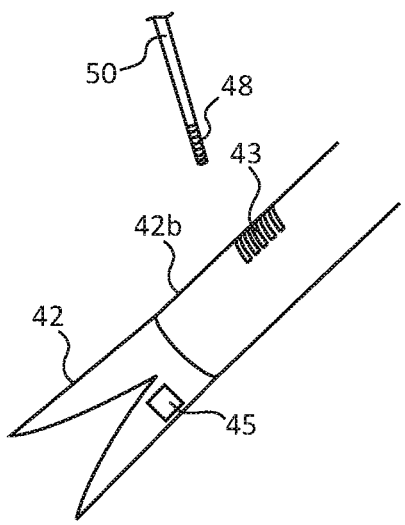
FIG. 2B is an enlarged view of the surgical instrument of FIG. 2A and an endoscope of the surgical robotic system of FIG. 1.

Referring to FIGS. 1, 2A, and 2B, a surgical system, such as, for example, a surgical robotic system 1, generally includes a plurality of surgical robotic arms 2, 3; an instrument drive unit 20 and an electromechanical instrument 10 attached to an end of the robotic arm 2; a control device 4; and an operating console 5 coupled with the control device 4. The operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 20, and thus electromechanical instrument 10 execute a desired movement according to a movement defined by means of manual input devices 7, 8. Control device 4 may also be set up in such a way that it regulates the movement of the robotic arms 2, 3 and/or movement of the drives.

Surgical robotic system 1 is configured for use on a patient "P" lying on a surgical table "ST" to be treated in a minimally invasive manner by means of a surgical instrument, e.g., electromechanical instrument 10. Surgical robotic system 1 may also include more than two robotic arms 2, 3, the additional robotic arms likewise being connected to control device 4 and being telemanipulatable by means of operating console 5. A surgical instrument, for example, an electromechanical surgical instrument 10 including an electromechanical end effector 42, may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control an imager 48 of the instrument drive unit 20 to drive movement and operation of the imager 48. The instrument drive unit 20 transfers power and actuation forces from its motors to driven members (not shown) of the electromechanical instrument 10 to ultimately drive movement of components of the end effector 42 of the electromechanical instrument 10, for example, a movement of a knife blade (not shown) and/or a closing and opening of jaw members of the end effector 42.

For a detailed description of the construction and operation of a robotic surgical system, reference may be made to U.S. Pat. No. 8,828,023, entitled "Medical Workstation," the entire contents of which are incorporated by reference herein.

With specific reference to FIGS. 2A and 2B, the surgical instrument 10 generally has a proximal end portion 42a configured to be engaged with the instrument drive unit 20 and a distal end portion 42b having the end effector 42 extending therefrom. The surgical instrument 10 further includes an elongate body or shaft 44. The end effector 42 extends distally from the distal end portion 42b of the elongate body 44 and is configured for performing a plurality of surgical functions. The surgical instrument 10 further includes a machine-readable representation of data, such as, for example, a barcode 43, disposed thereon, and a plurality of sensors 45 for determining a plurality of conditions of the surgical instrument 10, such as, for example, a clamping force between jaws of the end effector 42, a force required to articulate the end effector 42, a force required to rotate the end effector 42, and/or a force required to actuate a function of the end effector 42 (e.g., a stapling function). The sensors 45 may be force sensors and/or position sensors; however, other types of sensors are also contemplated.

It is contemplated that the surgical instrument 10 may be any suitable surgical instrument for performing a surgical task, such as, for example, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel sealing device, a vessel expanding device, a lumen expanding device, a scalpel, a fluid delivery device, monopolar or bipolar energy delivery devices (e.g., energized devices that can apply energy (heat, RF, etc.) to cut or coagulate tissue) or any other suitable type of surgical instrument, each of which being configured for actuation and manipulation by the surgical robotic system 1.

The surgical robotic system 1 may further include an imager 48, such as, for example, a camera or an imaging modality, configured to capture an image of the surgical instrument 10. The imager 48 may be positioned at any suitable location of the surgical robotic system 1, such as an endoscope 50 (FIGS. 1 and 2B), the instrument drive unit 20, or any suitable location within an operating room. The imager 48 may be any suitable imaging apparatus configured for still or moving imaging including, but not limited to, digital devices, such as charge-coupled device (CCD) camera, a complementary metal-oxide-semiconductor (CMOS) sensor, an active-pixel sensor (APS), and analog devices, such as a vidicon tube. In embodiments, the imager 48 may also include any suitable lens or optical apparatus (e.g., optical fiber) for transmitting light to the control device 4 (FIG. 1). The imager 48 may be in communication with the display device 6 (FIG. 1) for displaying the images captured thereby.

Figure 3:
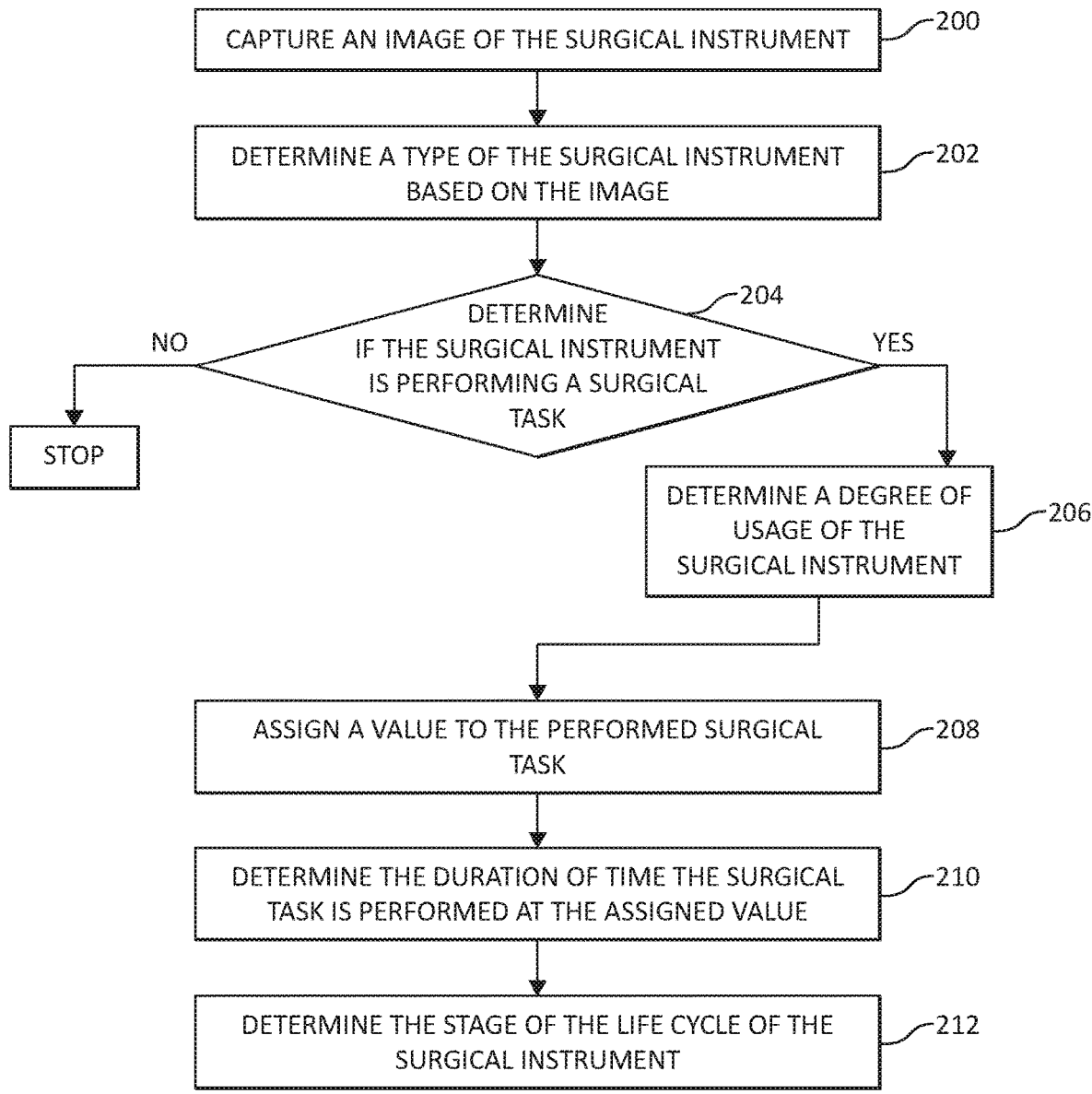
FIG. 3 is a flow chart illustrating a method of tracking usage of the surgical instrument of FIG. 2A.

With reference to FIG. 3, a method of tracking usage of the surgical instrument 40 using the surgical robotic system 1 will now be described. Each surgical instrument 40 may have a predetermined or pre-set life cycle. To determine the stage in the pre-set life cycle of the surgical instrument 40, the following method may be employed. In step 200, the control device 4 (FIG. 1) is configured to direct the imager 48 (FIGS. 2A and 2B) to capture an image or images of the surgical instrument 10 during a robotic surgical procedure. For example, the imager 48 may capture an image of the barcode 43, such that in step 202, the control device 4 may determine the type and identity of the surgical instrument 10 based on the image of the barcode 43 of the surgical instrument 10 captured by the imager 48. In some methods, the processor may have image data stored in a memory thereof of a variety of types of surgical instruments and may match the image taken of the surgical instrument 10 with an image stored in the memory of the processor to identify the type of the surgical instrument 10. It is contemplated that the control device 4 has a processor (not shown) capable of executing a series of instructions, algorithms, or protocols that are stored in a memory (e.g., a storage device and/or external device (not shown)) of the control device 4 for identifying the surgical instrument 10 based on the captured images thereof.

In step 204, the processor determines if and when the surgical instrument 10 is performing a surgical task based on the image of the surgical instrument 10 and/or based on forces sensed by the sensors 45 of the surgical instrument 10 and/or other sensors of the surgical robotic system 1. For example, if the image/video shows the surgical instrument 10 acting on tissue, such as closing the end effector 42 about the tissue, the processor determines that the surgical instrument 10 is performing a surgical task. In some methods, the processor may correlate the image/video with the forces sensed by the sensors 45 of the surgical instrument 10 or other sensors of the surgical robotic system 1 to determine/confirm that the surgical instrument 10 is performing a surgical task. In step 206, if it is determined that the surgical instrument 10 is performing a surgical task, the processor determines a degree of usage of the surgical instrument 10 based on data acquired by one or more of the sensors 45 of the surgical instrument 10 and/or other sensors of the surgical robotic system 1. In other embodiments, the degree of usage may be determined based on data acquired by the imager 48.

In step 208, the processor assigns a value to the surgical task performed by the surgical instrument 10 based on the amount of force applied to the tissue by the surgical instrument 10 during the surgical task. For example, the higher the force applied to the tissue by the surgical instrument 10, the higher the value assigned. In step 210, the processor determines a duration of time the surgical task is performed by the surgical instrument 10 at the value assigned to that surgical task. As such, the processor determines the degree of usage of the surgical instrument 10 based on how much time the surgical instrument 10 is being used at each discrete usage level. For example, in the case of an energy delivering surgical instrument 10, used to cut or coagulate tissue, the degree (amplitude) and time that the energy is delivered to tissue, may be a factor in calculating the degree of usage and/or life remaining for the energy delivering surgical instrument 10.

Accordingly, if during a first surgical task the surgical instrument 10 applies a relatively low force to tissue for a time (x), and during a second surgical task the surgical instrument 10 applies a relatively high force to tissue for a time (x), the degree of usage assigned to the second surgical task will be higher notwithstanding the duration of usage of both of the first and second surgical tasks being the same.

In step 212, the stage in a pre-set or predetermined life cycle of the surgical instrument 10 is determined based on the type of surgical instrument 10 identified and the degree of usage determined. The robotic surgical system 1 may display on a display device 6 (FIG. 1) the stage in the life cycle of the surgical instrument 10. It is contemplated that the stage in the life cycle may be displayed as a number, a percentage, a word, a color, a bar indicator, or using any other suitable indicia. Based on the stage in the life cycle of the surgical instrument 10, the clinician may choose to cease using the surgical instrument 10. In other embodiments, if the surgical instrument 10 is determined to be beyond its useful life (e.g., exceeded its predetermined life cycle), the surgical robotic system 1 may be configured to prevent further activation of the surgical instrument 10.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A method of tracking usage of a robotic surgical instrument, the method comprising:
    capturing an image of a surgical instrument with an imager during a robotic surgical procedure;
    identifying a type of the surgical instrument based on the image of the surgical instrument;
    during the robotic surgical procedure, determining a degree of usage of the surgical instrument based on data acquired by at least one sensor supported on jaws of the surgical instrument, wherein the degree of usage of the surgical instrument is a function of an amount of time of use of the surgical instrument and a function of forces measured by the at least one sensor during the time of use of the surgical instrument; and
    determining a stage in a life cycle of the surgical instrument based on the type of surgical instrument identified and the degree of usage determined during the robotic surgical procedure.

2. The method according to claim 1, further comprising determining if the surgical instrument is performing a surgical task based on the image of the surgical instrument.

3. The method according to claim 2, wherein determining if the surgical instrument is performing a surgical task includes correlating the image of the surgical instrument with the data acquired by the at least one sensor of the surgical instrument.

4. The method according to claim 2, wherein the surgical task includes the surgical instrument acting on tissue.

5. The method according to claim 4, wherein the degree of usage of the surgical instrument is determined only when the surgical instrument is acting on tissue.

6. The method according to claim 2, further comprising assigning a value to the surgical task performed by the surgical instrument corresponding to the degree of usage of the surgical instrument.

7. The method according to claim 6, wherein the value assigned to the surgical task performed by the surgical instrument is selected based on an amount of force applied to tissue by the surgical instrument during the surgical task.

8. The method according to claim 6, further comprising determining a duration of time the surgical task is performed by the surgical instrument at the assigned value.

9. The method according to claim 1, further comprising displaying on a display the stage in the life cycle of the surgical instrument.

10. A robotic surgical system, comprising:
a robotic arm;
a surgical instrument configured to be coupled to and operated by the robotic arm;
an imager configured to capture an image of the surgical instrument during a surgical procedure; and
a control device in communication with the imager and configured to:
   identify a type of the surgical instrument based on the image of the surgical instrument captured by the imager;
   during the robotic surgical procedure, determine a degree of usage of the surgical instrument based on data acquired by at least one sensor supported on jaws of the surgical instrument, wherein the degree of usage of the surgical instrument is a function of an amount of time of use of the surgical instrument and a function of forces measured by the at least one sensor during the time of use of the surgical instrument; and
   determine a stage in a life cycle of the surgical instrument based on the type of the surgical instrument identified and the degree of usage determined during the robotic surgical procedure.

11. The surgical robotic system according to claim 10, wherein the control device is further configured to determine if the surgical instrument is performing a surgical task based on the image of the surgical instrument.

12. The surgical robotic system according to claim 11, wherein the surgical task includes the surgical instrument acting on tissue.

13. The surgical robotic system according to claim 12, wherein the control device is configured to determine the degree of usage of the surgical instrument only when the surgical instrument is acting on tissue.

14. The surgical robotic system according to claim 12, wherein the control device is further configured to assign a value to the surgical task performed by the surgical instrument corresponding to the degree of usage of the surgical instrument.

15. The surgical robotic system according to claim 14, wherein the value assigned to the surgical task performed by the surgical instrument is selected by the control device based on an amount of force applied to tissue by the surgical instrument during the surgical task.

16. The surgical robotic system according to claim 14, wherein the control device is further configured to determine a duration of time the surgical task is performed by the surgical instrument at the assigned value.

17. The surgical robotic system according to claim 10, wherein the control device is further configured to display on a display the stage in the life cycle of the surgical instrument.

18. The surgical robotic system according to claim 10, wherein the imager includes an imaging modality.

19. The surgical robotic system according to claim 10, wherein the surgical instrument is a surgical stapler.

* * * * *